United States Patent
Hetke et al.

(10) Patent No.: US 8,800,140 B2
(45) Date of Patent: Aug. 12, 2014

(54) METHOD OF MAKING A MODULAR MULTICHANNEL MICROELECTRODE ARRAY

(75) Inventors: Jamille F. Hetke, Brooklyn, MI (US); Daryl R. Kipke, Dexter, MI (US); David S. Pellinen, Ann Arbor, MI (US); David J. Anderson, Ann Arbor, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 889 days.

(21) Appl. No.: 12/986,081

(22) Filed: Jan. 6, 2011

(65) Prior Publication Data
US 2011/0154655 A1    Jun. 30, 2011

Related U.S. Application Data

(63) Continuation of application No. 11/545,353, filed on Oct. 10, 2006, now Pat. No. 7,941,202.

(60) Provisional application No. 60/724,501, filed on Oct. 7, 2005.

(51) Int. Cl.
*H05K 3/02* (2006.01)

(52) U.S. Cl.
USPC ............. 29/846; 29/825; 29/842; 29/843; 29/878; 607/115

(58) Field of Classification Search
CPC .......... A61B 5/04001; A61B 2562/04; A61B 2562/0209; H05K 2201/0335; H05K 2201/0352; H05K 2201/0364; H05K 2201/0367
USPC ................... 29/825, 842, 843, 876, 878
See application file for complete search history.

(56) References Cited

U.S. PATENT DOCUMENTS

| | | |
|---|---|---|
| 3,847,687 A | 11/1974 | Davidsohn et al. |
| 3,921,916 A | 11/1975 | Bassous |
| 4,141,365 A | 2/1979 | Fischell et al. |
| 4,166,469 A | 9/1979 | Littleford |
| 4,306,562 A | 12/1981 | Osborne |
| 4,455,192 A | 6/1984 | Tamai |
| 4,461,304 A | 7/1984 | Kuperstein |
| 4,465,482 A | 8/1984 | Tittel |
| 4,762,135 A | 8/1988 | van der Puije |

(Continued)

FOREIGN PATENT DOCUMENTS

| | | |
|---|---|---|
| WO | 01/12115 | 2/2001 |
| WO | 02/36002 | 5/2002 |

(Continued)

OTHER PUBLICATIONS

Application No. PCT/IB06/53700, International Search Report mailed Nov. 21, 2008.

(Continued)

*Primary Examiner* — Carl Arbes
(74) *Attorney, Agent, or Firm* — Michael F. Scalise

(57) ABSTRACT

Some embodiments of the invention comprise a customizable multichannel microelectrode array with a modular planar microfabricated electrode array attached to a carrier and a high density of recording and/or stimulation electrode sites disposed thereon. Novel methods of making and using same are also disclosed.

20 Claims, 4 Drawing Sheets

(56) References Cited

U.S. PATENT DOCUMENTS

| | | | |
|---|---|---|---|
| 4,886,065 A | 12/1989 | Collins | |
| 4,904,237 A | 2/1990 | Janese | |
| 5,108,819 A | 4/1992 | Heller et al. | |
| 5,180,376 A | 1/1993 | Fischell | |
| 5,207,709 A | 5/1993 | Picha | |
| 5,215,088 A | 6/1993 | Normann et al. | |
| 5,308,442 A | 5/1994 | Taub et al. | |
| 5,322,064 A | 6/1994 | Lundquist | |
| 5,385,635 A | 1/1995 | O'Neill | |
| 5,390,671 A | 2/1995 | Lord | |
| 5,409,469 A | 4/1995 | Schaerf | |
| 5,496,360 A | 3/1996 | Hoffmann et al. | |
| 5,515,848 A | 5/1996 | Corbett, III et al. | |
| 5,524,338 A | 6/1996 | Martyniuk et al. | |
| 5,573,520 A | 11/1996 | Schwartz et al. | |
| 5,585,827 A | 12/1996 | Murakami | |
| 5,588,597 A | 12/1996 | Reinecke et al. | |
| 5,720,099 A | 2/1998 | Parker et al. | |
| 5,744,958 A | 4/1998 | Werne | |
| 5,800,535 A | 9/1998 | Howard, III | |
| 5,843,150 A | 12/1998 | Dreessen et al. | |
| 5,927,277 A | 7/1999 | Baudino et al. | |
| 5,938,694 A | 8/1999 | Jaraczewski et al. | |
| 5,975,085 A | 11/1999 | Rise | |
| 5,989,445 A | 11/1999 | Wise et al. | |
| 5,992,769 A | 11/1999 | Wise et al. | |
| 6,006,124 A | 12/1999 | Fischell et al. | |
| 6,016,449 A | 1/2000 | Fischell et al. | |
| 6,044,304 A | 3/2000 | Baudino | |
| 6,132,456 A | 10/2000 | Sommer et al. | |
| 6,181,569 B1 | 1/2001 | Chakravorty | |
| 6,205,361 B1 | 3/2001 | Kuzma et al. | |
| 6,228,111 B1 | 5/2001 | Tormala et al. | |
| 6,304,787 B1* | 10/2001 | Kuzma et al. | 607/137 |
| 6,324,433 B1 | 11/2001 | Errico | |
| 6,325,797 B1 | 12/2001 | Stewart et al. | |
| 6,374,143 B1 | 4/2002 | Berrang et al. | |
| 6,430,443 B1 | 8/2002 | Karell | |
| 6,600,231 B2 | 7/2003 | Tominaga | |
| 6,618,623 B1 | 9/2003 | Pless et al. | |
| 6,757,970 B1* | 7/2004 | Kuzma et al. | 29/847 |
| 6,829,498 B2 | 12/2004 | Kipke et al. | |
| 6,834,200 B2 | 12/2004 | Moxon et al. | |
| 6,878,643 B2 | 4/2005 | Krulevitch et al. | |
| 7,004,948 B1 | 2/2006 | Pianca et al. | |
| 7,006,859 B1 | 2/2006 | Osorio et al. | |
| 7,010,356 B2 | 3/2006 | Jog et al. | |
| 7,011,680 B2 | 3/2006 | Alt | |
| 7,089,059 B1 | 8/2006 | Pless | |
| 7,181,288 B1 | 2/2007 | Rezai et al. | |
| 7,244,150 B1* | 7/2007 | Brase et al. | 439/668 |
| 7,343,205 B1 | 3/2008 | Pianca et al. | |
| 7,451,000 B2* | 11/2008 | Gibson et al. | 607/137 |
| 7,548,775 B2 | 6/2009 | Kipke et al. | |
| 7,871,707 B2 | 1/2011 | Laude et al. | |
| 7,914,842 B1 | 3/2011 | Greenberg et al. | |
| 7,941,202 B2 | 5/2011 | Hetke et al. | |
| 8,620,459 B2* | 12/2013 | Gibson et al. | 607/137 |
| 8,660,665 B2* | 2/2014 | Walter et al. | 607/117 |
| 2001/0049499 A1 | 12/2001 | Lui et al. | |
| 2002/0029074 A1* | 3/2002 | Treaba et al. | 607/137 |
| 2002/0052610 A1 | 5/2002 | Skakoon et al. | |
| 2002/0183817 A1 | 12/2002 | Van Venrooij et al. | |
| 2002/0198446 A1 | 12/2002 | Hill et al. | |
| 2003/0093129 A1 | 5/2003 | Nicolelis et al. | |
| 2003/0100823 A1 | 5/2003 | Kipke | |
| 2003/0114906 A1 | 6/2003 | Booker et al. | |
| 2003/0187461 A1 | 10/2003 | Chin | |
| 2004/0006264 A1 | 1/2004 | Mojarradi et al. | |
| 2004/0030376 A1* | 2/2004 | Gibson et al. | 607/137 |
| 2004/0102828 A1 | 5/2004 | Lowry et al. | |
| 2004/0106169 A1 | 6/2004 | Evans | |
| 2004/0199235 A1 | 10/2004 | Younis | |
| 2005/0004627 A1 | 1/2005 | Gibson et al. | |
| 2005/0021116 A1 | 1/2005 | He et al. | |
| 2005/0021117 A1 | 1/2005 | He et al. | |
| 2005/0137647 A1 | 6/2005 | Wallace et al. | |
| 2005/0222647 A1 | 10/2005 | Wahlstrand et al. | |
| 2006/0122677 A1 | 6/2006 | Vardiman | |
| 2006/0173263 A1 | 8/2006 | He et al. | |
| 2006/0247749 A1 | 11/2006 | Colvin | |
| 2006/0258951 A1 | 11/2006 | Bleich et al. | |
| 2006/0276866 A1 | 12/2006 | McCreery | |
| 2006/0282014 A1 | 12/2006 | Kipke et al. | |
| 2007/0073130 A1 | 3/2007 | Finch et al. | |
| 2007/0123765 A1 | 5/2007 | Hetke et al. | |
| 2007/0135885 A1* | 6/2007 | Risi | 607/137 |
| 2008/0132970 A1 | 6/2008 | Barolat | |
| 2008/0208283 A1 | 8/2008 | Vetter et al. | |
| 2008/0255439 A1 | 10/2008 | Tang et al. | |
| 2008/0262584 A1 | 10/2008 | Bottomley et al. | |
| 2009/0099555 A1 | 4/2009 | Viohl et al. | |
| 2009/0102068 A1 | 4/2009 | Pellinen et al. | |
| 2009/0118806 A1 | 5/2009 | Vetter et al. | |
| 2009/0132042 A1 | 5/2009 | Hetke et al. | |
| 2009/0149934 A1 | 6/2009 | Ameri et al. | |
| 2009/0171421 A1 | 7/2009 | Atalar et al. | |
| 2009/0187196 A1 | 7/2009 | Vetter | |
| 2009/0234426 A1 | 9/2009 | Pellinen et al. | |
| 2009/0240314 A1 | 9/2009 | Kong et al. | |
| 2009/0248118 A1 | 10/2009 | Bradley et al. | |
| 2009/0253977 A1 | 10/2009 | Kipke et al. | |
| 2009/0299167 A1 | 12/2009 | Seymour | |
| 2009/0312770 A1 | 12/2009 | Kozai et al. | |
| 2010/0030298 A1 | 2/2010 | Martens et al. | |
| 2010/0145216 A1 | 6/2010 | He et al. | |
| 2010/0145422 A1 | 6/2010 | Seymour et al. | |
| 2011/0093052 A1 | 4/2011 | Anderson et al. | |

FOREIGN PATENT DOCUMENTS

| | | |
|---|---|---|
| WO | 0241666 | 5/2002 |
| WO | 02/96482 | 12/2002 |
| WO | 2005/039696 | 5/2005 |
| WO | 2006138358 A | 12/2006 |
| WO | 2007042999 A | 4/2007 |
| WO | 2007089738 A | 8/2007 |
| WO | 2008011721 A | 1/2008 |
| WO | 2008038208 A | 4/2008 |
| WO | 2008072125 A | 6/2008 |
| WO | 2008109298 A | 9/2008 |
| WO | 2009052423 A | 4/2009 |
| WO | 2009052425 A | 4/2009 |
| WO | 2010057095 A | 5/2010 |
| WO | 2011/010257 | 1/2011 |
| WO | 2011046665 A | 4/2011 |

OTHER PUBLICATIONS

Application No. PCT/IB10/53250, International Search Report mailed Oct. 4, 2010.
Application No. PCT/US04/35030, International Search Report mailed Feb. 21, 2005.
Application No. PCT/US06/23139, International Search Report mailed Aug. 2, 2007.
Application No. PCT/US07/02465, International Search Report mailed Feb. 13, 2008.
Application No. PCT/US08/55025, International Search Report and Written Opinion mailed Oct. 27, 2008.
Application No. PCT/US08/80364, International Search Report and Written Opinion mailed Dec. 16, 2008.
Application No. PCT/US08/80366, International Search Report and Written Opinion mailed Dec. 10, 2008.
Application No. PCT/US09/64591, International Search Report and Written Opinion mailed Jul. 21, 2010.
Application No. PCT/US10/44167, International Search Report and Written Opinion mailed Sep. 27, 2010.
Lin et al., "Silicon Processed Microneedles," IEEE J. Micro. Electro. Mech. Sys, vol. 8, No. 1 (1999) 78-84 (7 pages).
U.S. Appl. No. 12/986,081, Hetke.
Seymour, John P., Kipke, Daryl R. "Neural probe design for reduced tissue encapsulation in CNS", 28 (2007) 3594-3607, Apr. 5, 2007.

(56) References Cited

OTHER PUBLICATIONS

Seymour, John P., Elkasabi, Yaseen M., Chen, Hsien-Yeh, Lahann, Joerg, Kipke, Daryl R., "The insulation performance of reactive parylene films in implantable electronic devices", Biomaterials 30 (2009) 6158-6167, Aug. 22, 2009.

Kaplan, et al., "A Novel Fabrication Method of Capillary Tubes on Quartz for Chemical Analysis Applications", IEEE Proceedings, Micro Electro Mechanical Systems, Jan. 25-28, 1994.

Lin, et al., "Silicon Processed Microneedles", The 7th International Conference on Solid State Sensors and Acutators; Jun. 7-10, 1993.

* cited by examiner

METHOD OF MAKING A MODULAR MULTICHANNEL MICROELECTRODE ARRAY

CROSS-REFERENCE TO RELATED APPLICATIONS

This application is a continuation of and claims the benefit of prior U.S. patent application Ser. No. 11/545,353, filed Oct. 10, 2006, which claims priority based on U.S. Provisional Patent Application No. 60/724,501, filed Oct. 7, 2005, which are both hereby incorporated by reference in full.

FIELD OF THE INVENTION

The invention relates to the field of devices and methods used for neural interventions.

BACKGROUND

Neurosurgical interventions are emerging as treatments for a variety of intractable neurological conditions, including among them, movement disorders, pain, and epilepsy. Different modalities of treatment that target discrete anatomical sites are in current use or in development, including radiofrequency lesioning, chronic electrical stimulation, tissue implantation, and microdialysis. The strategy of these interventions is to diminish or enhance the activity of these sites so as to produce a therapeutic effect. In all cases, accurate targeting is essential to obtain an optimal treatment with minimal risk to the patient.

Targeting is often effected through devices that establish a neural interface. Such devices are important for clinical and scientific purposes. A 'neural interface' refers to the interface between a device and a targeted region of the nervous system for the purposes of recording neural signals, stimulating neurons, and delivering fluidic agents, or combinations of these purposes. A 'neural interface region' refers to the volume of the nervous system that is recorded from, stimulated, or affected by delivery of the fluidic agent. In general, neural interface regions could extend from as small as 1 micron or less from the device surfaces to several centimeters from the surfaces, depending on the application. 'Tuning' the neural interface region refers to selectively adjusting the recording, stimulation, or fluid delivery regions to target specific neural structures.

As only one example, a current method for targeting for placement of a deep brain stimulation ("DBS") electrode for Parkinson's Disease involves the use of neurophysiological (functional) mapping of structure boundaries with reference to high quality CT or MRI images of the brain. At present, mapping involves penetrating the computed target structures with single-channel movable wire microelectrodes to identify the neuronal structure boundaries. Each microelectrode is advanced very slowly, stopping to examine individual cells and to record the firing frequency and pattern. When the microelectrode reaches the target brain structure, a typical change in electrical activity occurs, due to the sustained pattern of discharge of specific neuron types.

In addition to using electrical recording techniques for mapping, macro- or microstimulation (from the same or a second adjacent electrode) can be used to assess the effects of electrical stimulation on units along the trajectory and in the potential target. Specifically, combined microrecording and microstimulation techniques can be used to physiologically determine the location of both target and non-target areas deep within the brain. Due to limitations related to the electrode, which is typically a single-channel device or a number of single-channel devices used together, this mapping procedure is often tedious, time-consuming, and difficult, which combine to limit its utilization and effectiveness.

Conventional single-channel electrodes are typically formed from small diameter metal wires (e.g., tungsten, stainless steel, platinum). These electrodes are most often formed by electrolytically sharpening or mechanically beveling the wire to a fine tip (<1 micrometer) and then insulating it, leaving only the tip exposed. Alternatively, microwires can be formed from pre-insulated fine wires that have been cut to expose the cross-sectional area at the end of the wire. These types of wire devices can be converted into electrode arrays by combining multiple wires into an assembly. However, this bundled wire construction creates limitations to establishing selective neural interfaces because the size, number, and location of electrode sites are intricately related to the device's size, shape, stiffness, and structural complexity. Such devices are also difficult to manufacture to small tolerances on the order of an electrode site feature size, typically in the range of 1-15 microns. The relatively large variability in electrode size and the limited electrode array configurations of these devices preclude the ability to connect groups of electrodes together to selectively tune the neural interface.

As an alternative to bundled wires, multichannel electrode arrays that utilize wafer-level microfabrication methods employed in the semiconductor industry have been under development for nearly three decades (Wise, et al., 2004, Proc. IEEE, 92:72-97) and have been used for neurophysiological research. In general, these techniques are similar to those used to create integrated circuits and utilize similar substrate, conductor, and insulating materials. Fabrication typically starts on a wafer substrate, and the electrode features are added using a number of photolithographically patterned thin-film layers that are defined by etching. These methods are attractive since they result in reproducible, batch-processed devices that have features defined to within less than +/−1 micron. Using these methods, an individual electrode site can be made about as small as the tip of a small wire microelectrode, while the microelectrode shank, the portion that supports the electrode sites and displaces the tissue, can carry multiple recording sites and can cross-sectional area and volume that is comparable to a single wire electrode.

Generally speaking, the fabrication processes for current microfabricated devices impose practical limits on the length of the device to about less than 1 cm. Such a device would not be suitable, for example, for a human deep brain mapping electrode which must penetrate at least 70 mm from the brain surface to target the basal ganglia or thalamus. In addition, these mapping electrodes require extra length of up to 200 mm for mounting in a stereotactic frame and for connection to external instrumentation. Another limitation to microfabricated devices is that the materials typically used as a substrate are often either too brittle (e.g. silicon) or too flexible (e.g. polyimide, parylene) to precisely target particular neural structures.

There are examples of multi-site devices for neural interfacing that do not use wafer level microfabrication techniques but that do employ similar processing steps such as thin-film metal deposition and subsequent laser micromachining to define electrode traces on a central core. While these devices may provide a high density of sites on a substrate similar in size to conventional single-channel wires, and they can be manufactured on substrates that can target human deep brain, there are several desirable characteristics that are absent. First, the devices are not batch fabricated. In other words, each device must be treated individually to form a plurality of electrode interconnects and sites. Additionally, in many cases, each interconnect as well as each site must be individually formed. Second, the array of electrode sites and interconnects are built up from the structural substrate in a manner that generally makes the formation of the electrical features (e.g. sites, traces and connection contacts) closely dependent on the length, shape, and material properties of the substrate. The coupling between formation and placement of the electrode sites and the underlying structural component limits the ability to group small sites to form a macro site to shape the interface range.

There exist examples of devices used for clinical deep brain mapping, which are designed for intraoperative use only. These consist of a single microelectrode site that is appropriate in size for neurophysiological mapping. While these electrodes have enabled improved placement of deep brain stimulation electrodes, they only offer recording capability at the tip, limiting the capability to tune the region with which the device is interfaced.

There are also examples of devices used for clinical DBS, which are designed for long-term implantation and functionality. These devices are comprised of a flexible polymer cylindrical substrate with four metal electrode contacts (sometimes referred to as "macroelectrodes"). These electrode contacts are configured such that each electrode site is placed around the perimeter of a flexible substrate to form a cylindrical shape. The electrode sites are positioned linearly along the axis of the cylindrical substrate. Due to the relatively large size of this device (including its stimulating surfaces), the small number of stimulating sites, and the way that it is constructed, this device is limited in its ability to establish tunable neural interface regions.

The ability to record and/or stimulate, for example, through multiple electrode sites simultaneously has the potential to greatly improve the speed and accuracy of the mapping procedure. While single site electrodes are limited by permitting recording from only a single point in tissue at a time, electrodes with multiple spatially separate recording channels would be capable of recording simultaneously from many points. Recordings may be comprised of spontaneous neuronal activity, movement-related activity, or evoked activity as a result of stimulation from nearby sites. Simultaneously sampled recordings could be exploited to increase the speed and accuracy by which data are acquired. Electrode arrays that are capable of simultaneously sampling from the same neuronal region are also likely to detect regions of statistically independent background noise and/or artifacts. Using advanced signal processing techniques such as independent component analysis, these unwanted signals could be identified and removed, resulting in improvement of the signal-to-noise ratio, and in turn facilitating neuronal spike discrimination. This technique may also reveal signals that were previously hidden within the background noise. Thus, an unmet need remains for a neural interface device that:

- Can be configured to create selective and tunable neural interface regions over large spatial distances;
- Establishes high-resolution multi-site interfaces targeted at all regions of the nervous system (e.g., centrally or peripherally), including deep brain regions;
- Establishes multi-modal (e.g., electrical and chemical) interfaces targeted at all regions of the nervous system (centrally or peripherally), including deep brain regions;
- Has a large design space (e.g., site area, site spacing, substrate shape) to provide customizable devices specific to a variety of applications;
- Is capable of supporting a high density of electrode sites on a substrate/carrier that is the same size or smaller than conventional single-channel microelectrodes;
- Is fabricated from biocompatible materials; and
- Is easily manufactured.

SUMMARY

Without limitation to only embodiments described in this section, the invention comprises a modular multichannel microelectrode array (also "neuroprobe system") having a carrier with at least one planar microelectrode array attached to the carrier, the planar microelectrode array comprising a substrate formed separately from the carrier and further comprising a plurality of interconnects disposed on the substrate between layers of dielectric material, a plurality of electrode sites at least some of which are in contact with a corresponding interconnect, and a plurality of bond pads at least some of which are in contact with a respective interconnect, wherein at least one of the electrode sites is a recording site or a stimulation site. Methods of making and using same are also disclosed herein, as are additional features of these and other embodiments.

BRIEF DESCRIPTION OF THE DRAWINGS

The present invention will now be described, by way of example only, with reference to the accompanying drawings, in which.

Other aspects of the invention will be apparent to those skilled in the art after reviewing the drawings and the detailed description below.

DETAILED DESCRIPTION

Without limiting the invention to only those embodiments described specifically herein, some embodiments comprise a multichannel neuroprobe that is modular and customizable and that can be used in a variety of configurations for micro- and macro-level interfacing with targeted neural populations. The neuroprobe is comprised of a central carrier onto which a planar multichannel microelectrode array is attached. The device and methods of making same use semiconductor microfabrication techniques to achieve precise, small features that can be optimized to interface with specific brain structures, and novel assembly techniques to convert the microfabricated array into a macro-scale structure that can be used to reach a variety of central and peripheral nervous system regions.

Figure 1:
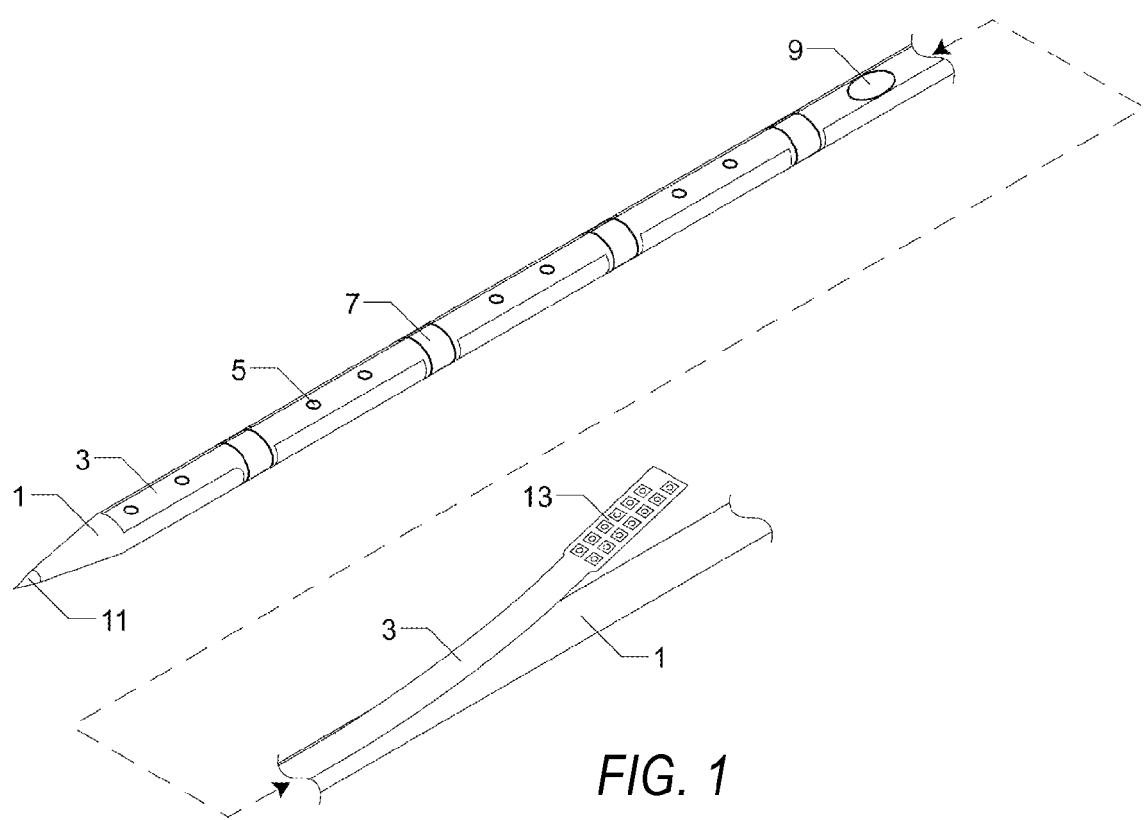
FIG. 1 illustrates the distal and proximal ends of a preferred embodiment of the neuroprobe system

Some embodiments of the invention comprise (FIG. 1):

1. A cylindrical carrier 1 that can either be rigid or flexible, solid or hollow, depending on material choice and desired use, and
2. A planar microfabricated electrode array 3 attached to the carrier 1 that offers a high density of microelectrode sites 5, 7, 9 at the distal end and bonding regions 13 at the proximal end.

The microelectrode array component can be custom designed to optimally sample (record) and/or selectively activate (stimulate) neural populations. Embodiments comprise the ability to selectively tune the size and shape of the neural interface region that is to be recorded from and/or stimulated. Sites can be tuned for recording, stimulation, or the substrate can include a combination of both types of sites that can be used, as one example only, for applications such as impedance measurement of tissue (e.g. Siemionow, *J. Neurosci. Meth.*, 2000, 96:113-117).

The carrier provides structural support and, in some embodiments, extends the functionality of the device by providing a lumen through which fluids (e.g. those containing pharmaceutical compounds) can be delivered to targeted structures, and/or by additional function as a single-channel microelectrode.

In some embodiments, without limitation (FIG. 1), the neuroprobe system is comprised a planar microelectrode array 3 disposed on an insulated metal wire (e.g. tungsten, stainless steel, platinum-iridium) carrier 1. Optionally the distal end of the wire carrier can be sharpened and the insulation can be removed at the tip 11 to form a conventional single-channel microelectrode. This configuration makes the device a drop-in replacement for current human deep brain mapping electrodes, for example, with extended functionality (i.e. multichannel recording and/or stimulation). In another embodiment, the planar microelectrode array 3 is disposed on a flexible polymeric (e.g. polyimide, silicone) carrier. Optionally the carrier can include a lumen and a port at its distal end that can be used for targeted drug delivery. This feature allows for the precise delivery of specific pharmaceutical compounds to localized regions of the nervous system which could assist, for example, with intraoperative mapping procedures or with long-term therapeutic implant devices. Optionally a stiffener or stylet is inserted through the lumen to facilitate assembly and insertion of the neuroprobe into the target tissue. This stiffener or stylet may be removed after insertion if the device is to be used in a permanent manner or if the lumen is to be used for drug delivery. If the stiffener or stylet is a sharpened, insulated metal wire with the insulation removed at the tip, it can be used as a conventional single-channel microelectrode as previously described.

The planar microelectrode array 3 is comprised of conductive interconnects disposed between layers of dielectrics which insulate the interconnects on top and bottom sides. At least some interconnects terminate with recording and/or stimulation electrode sites 5, 7, 9 on the distal end and/or with bond pads 13 for electrical connection to external instrumentation and/or hybrid chips on the proximal end. In one embodiment, the interconnects are metal (e.g. platinum, gold) and the dielectric is a polymer (e.g. polyimide, parylene, PDMS). In another embodiment, the interconnects are polysilicon insulated with inorganic dielectrics (e.g. $SiO_2$, $Si_3N_4$) and polymer. In another embodiment, the interconnects are polysilicon insulated with inorganic dielectrics that are supported below by a silicon substrate. In yet another embodiment, the device is either a silicon or polymer-based structure with electrode sites, interconnects and bond pads as described above, as well as a buried channel for fluid delivery (e.g. Chen, et al., 1997, *IEEE Trans. Biomed. Engin.*, 44:760-769; Takeuchi, et al, *Proceeding of IEEE International Micro Electro Mechanical Systems* (MEMS'04), pp. 208-210 (2004)).

Electrode sites and bond pads are formed by opening apertures through the top dielectric and depositing and patterning metal (e.g. iridium, platinum, gold). In one embodiment, electrode sites 5, 9 are located on the distal end of the main body of the planar microelectrode array. At least one of these electrode sites 9, for example, can be larger in area and used as a reference site for recording or stimulation. In another embodiment, the array also has electrode sites on "tabs" 7 that project off the side of its main body. These tab sites 7 can be used to form ring electrodes that wrap around the carrier that can be used for stimulation and/or recording.

The precision, consistency, and reproducibility of the electrode sites on the microelectrode array result in predictable electrical and spatial characteristics. These characteristics enable the sites to be grouped in a manner that enables precise, predictable, and selective tuning of neural interface regions. Some embodiments of the invention comprise two or more electrode sites grouped to form a larger composite site that enables tuning the neural interface region for recording and/or stimulation. This grouping of sites can be through intrinsic connection of the site traces, or it can be through external connections for 'on the fly' tuning.

The composite sites can have diverse shapes that are driven by desired requirements of the neural interface. For example, a composite site may be a vertical strip along the array or a horizontal band. It may also tie together opposing strips to form a contiguous band. Composite sites can be used to establish one or more tunable neural interface region for the device. Multiple neural interface regions can be overlapping or non-overlapping.

The composite sites have utility for recording and/or electrical stimulation. For stimulation, a larger composite site increases the effective site area to allow increased charge injection while maintaining safe electrochemical and biological limits. This will enable, for example, precise current steering to selectively stimulate neural structures. For recording, a composite site can be used to change the recording selectivity of the device to emphasize, for example, field potential recording over single-unit recordings.

General fabrication techniques of these planar polymer and silicon microelectrode arrays are known to those skilled in the art (e.g., Rousche, et al., *IEEE Trans. Biomed. Engin.*, 48:361-371, Hetke, et al., 1994, *IEEE Trans. Biomed. Engin.*, 41:314-321). In addition, embodiments of the invention include novel processing and design modifications that make the novel planar microelectrode array component, as outlined below.

It is important to keep the width of the planar microelectrode array 3 within certain limits so that the assembled neuroprobe system (FIG. 1) is comparable in size to a conventional single-channel microelectrode (e.g. commercially available single-channel deep brain mapping microelectrodes are typically less than about 330 microns in diameter near the tip). Yet it is also critical to have the capability to include large electrode site 5, 7, 9 areas for some applications. One method to keep the width minimized is to provide two layers of interconnects, each layer being separated by a layer of dielectric. This permits more densely packed interconnects in a given width. Another method to minimize width involves a novel electrode site formation process. Existing techniques for producing electrode sites on polyimide and parylene substrates use a single step process that involves etching an aperture through the top dielectric to expose the metal site below. In such cases, the electrode site is contiguous with the interconnect and the result is an electrode site that is recessed within the top dielectric. Depending on the desired site area and shape, the metal typically widens in the region of the site aperture resulting in a scaling of substrate width with electrode site size.

Figure 2:
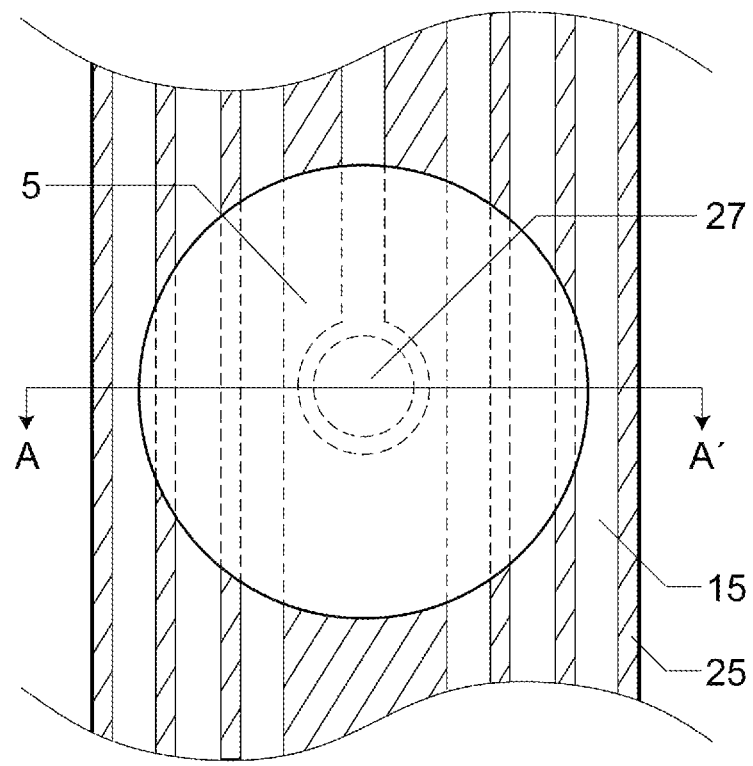
FIG. 2 illustrates the electrode site formation process
Figure 2:
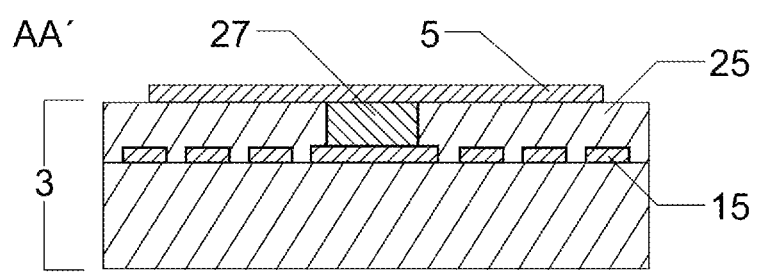

In a polymeric microelectrode array embodiment, without limitation, electrode sites are formed using a three step process which results in a site area that is not limited to or defined by the size of the aperture through the top dielectric (FIG. 2). First, a small site aperture is etched through the top dielectric

25 using reactive ion etching ("RIE"). The recess is next filled by electroplating metal (e.g. gold, platinum) 27 through a photolithographically defined mask. Finally, metal is deposited and the electrode site 5 is formed using a conventional lift-off process. As illustrated in FIG. 2, the site 5 is not limited by the size of the aperture. In fact, it can be much larger than the aperture since it is electrically isolated from underlying interconnects 15 by dielectric 25. In addition, it can have virtually any desired shape. Using this method, for example, at least twelve electrode sites and associated metal interconnects can be realized on a polyimide substrate that is 180 microns wide. The electrode sites can have a diameter of up to the 180 micron substrate width.

Figure 3:
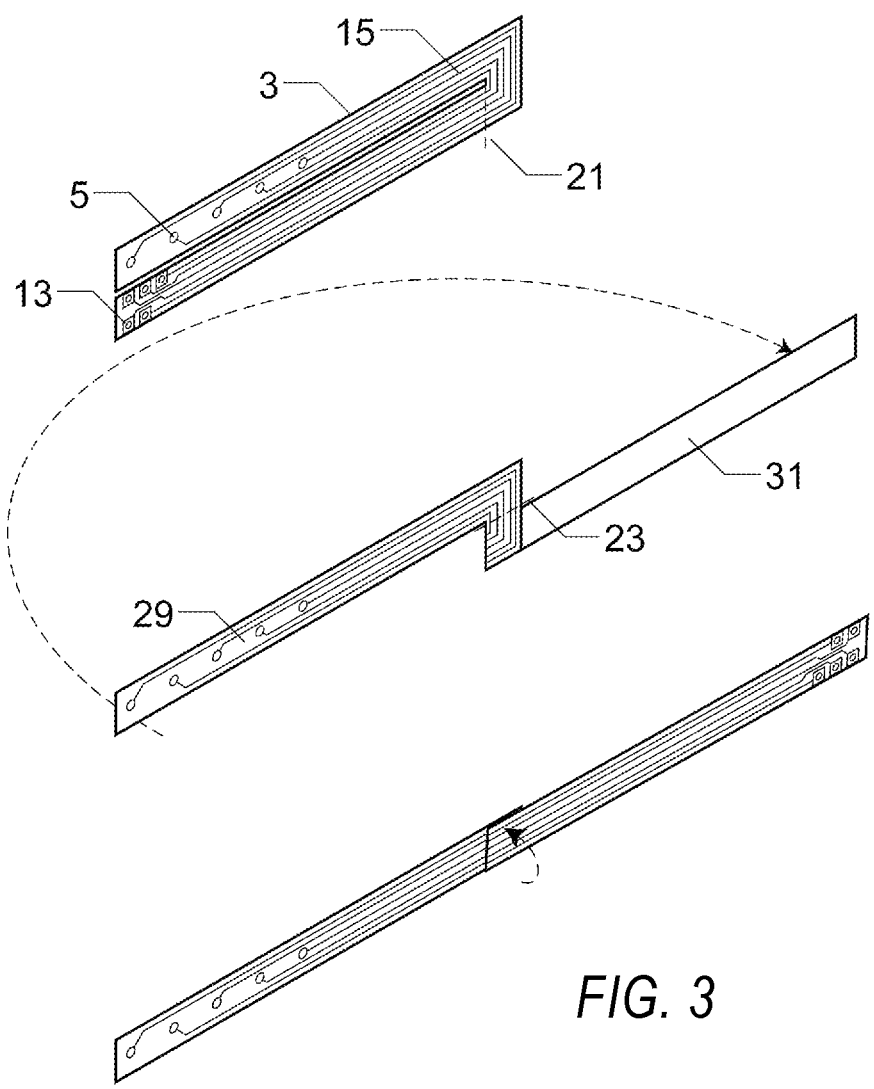
FIG. 3 illustrates the method used for folding the polymer arrays to achieve long lengths

Since, before the invention, the length of a planar microelectrode array was usually limited by the diameter of the wafer on which it is fabricated (typically 4 or 6 inches in diameter), one of several techniques must be used to achieve lengths longer than this. If the array dielectric material is polyimide, the arrays can be designed in a serpentine shape (FIG. 3) that can be folded into long, straight structures suitable for mounting on long carriers. The folding process is illustrated in FIG. 3. To perform the first fold, one segment 29 is stabilized while the other segment 31 is flipped under and then crimped down at the fold line 21. This crimping process can be performed using a polished surface such as a glass slide or metal block. The second fold is performed by flipping the second segment 31 up and then crimping the device at the fold line 23 to achieve the final straight shape. To ensure that the device holds its shape, it can be clamped in place and tempered at about 340° C. for about two hours. Using this method, as one example only, a 280 mm long device suitable for recording or stimulating from human deep brain can be realized using four 70 mm long segments connected by three folding regions.

In embodiments of the planar microelectrode array that include parylene, inorganic dielectrics, and/or silicon, the device cannot be folded and crimped due to material properties. In this case, a two stage device can be assembled that is comprised of the microelectrode array which will interface with neural tissue, and a foldable polyimide cable to transfer signals to/from the array. This polyimide cable has the same basic structure as the polyimide microelectrode array described above but has bond pads on both its distal (for connecting to the alternative microelectrode array) and proximal (for connecting to external instrumentation) ends. The two components can be coupled by methods known to those of ordinary skill in the art, as one example only, the Microflex Interconnect Technique outlined in Meyer, et al., 2001, *IEEE Trans. Adv. Packaging*, 24:366-375. Exposed connections can be insulated by molding the device into a polymeric (e.g. silicone) structure that will also serve as the carrier.

As described herein, bond pads are provided at the proximal end of the planar microelectrode array to provide a method for electrically contacting the array so that recorded signals can be accessed and/or so that stimuli may be provided. These pads can be bonded to a connector assembly (typically a form of printed-circuit board with or without on-board integrated circuits and a connector), or they can be connected directly to an Application Specific Integrated Circuit (ASIC). An example of an application for the latter case would be a multiplexer chip to reduce lead count, or a buffer amplifier to reduce signal loss over long leads.

The ability to combine microelectrode and macroelectrode sites on a single device allows for sites to be used in a customized mode of operation. The positions of the sites selected for stimulation can be adjusted as needed to optimally interface with the neural region of interest. This allows for sites to be configured to create an optimized arrangement of anode and cathode configurations. Additionally, sites can be used on an individual basis or as a group to effectively form a single macroelectrode comprised of a plurality of microelectrodes. This is of particular importance for stimulation, providing an additional degree of freedom when tuning the stimulation parameters in order to optimally interface with the targeted neural region. For example, electrode sites can be configured in a way that the grouped sites effectively form a vertical "strip" electrode or alternatively configured to effectively form a "band" electrode. In addition, grouping sites together can increase the charge delivery capability. This flexibility allows a user the option to span the range from microstimulation to macrostimulation with an increased level of spatial resolution.

Assembly of some embodiments of the neuroprobe system is described here. The proximal end of the folded microelectrode array component and its associated connector are first attached to the carrier with a suitable medical grade epoxy (e.g. Epoxy Technologies 353-NDT). The distal end of the microelectrode array component can be temporarily attached to the carrier using a water soluble epoxy (e.g. Master Bond MB-600) to facilitate the following step. A double-sided device can be realized by attaching a second array on the opposing side of the carrier). The distal end of the microelectrode array/carrier assembly is next threaded into a shorter length of medical grade micro shrink tube (e.g. polyester, PTFE, FEP). It is threaded through until it emerges from the other end of the shrink tube so that the conductive electrode sites are exposed. The assembly is then heated to activate the shrink tube, holding the microelectrode array and its associated folds tight to the carrier. The water soluble epoxy that holds the distal end(s) of the microelectrode array component(s) to the carrier should now be removed by soaking the distal end in water for several seconds.

There are several suitable methods to permanently attach the distal end of the microelectrode array component to the carrier. The first involves application of a very thin layer of medical grade adhesive to the carrier (e.g. Epoxy Technologies 377). This can be done by one of several methods which include, but are not limited to:

Dip-coating—In this procedure the distal end of the microelectrode array is held away from the carrier and the carrier is dipped into epoxy and pulled back out to leave a thin layer of epoxy. The microelectrode array is then placed onto this epoxy. Note that if the carrier is of the hollow tubing type that the proximal end must be first sealed off to avoid wicking of epoxy up into the lumen. The seal can be cut off during one of the final assembly steps.

Painting—As an alternative to dip coating which coats the entire surface, a small tool such as a pulled glass micropipette can be used to selectively coat the carrier by "painting".

Dispensing using adhesive dispenser—There are a number of commercially available adhesive dispensers (e.g. EFD 2400) that dispense microdots or lines of adhesive.

Figure 4A:
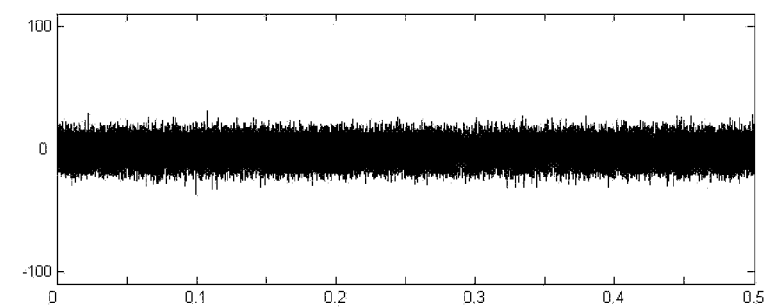
FIG. 4 shows electrical recordings from the neuroprobe system acquired from saline and brain tissue.
Figure 4B:
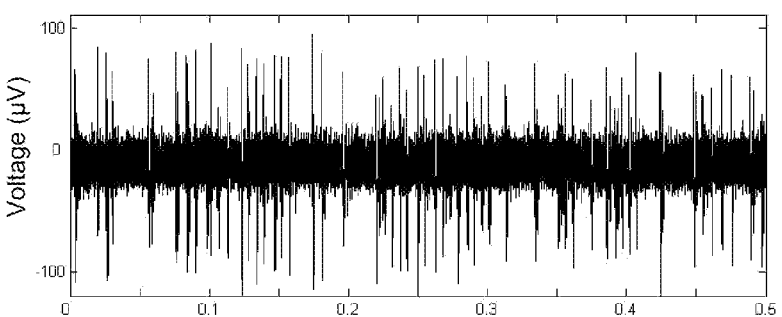

FIG. 4 illustrates the recording functionality of one embodiment of the neuroprobe system comprised of a polyimide microelectrode array attached to a polyimide tube with a tungsten stylet. The polyimide array was about 280 mm long and had recording platinum recording sites that had a surface area of about 1000 microns$^2$. The device was evaluated both on the bench top and in animals. Bench top tests were conducted by delivering a previously acquired neural recording into saline and subsequently recording this signal with the neuroprobe system. A recorded neural (voltage) waveform was converted into a current waveform using an optically isolated current stimulator. This signal was then delivered into saline through a bipolar electrode made from twisted platinum wire (each wire was 200 microns in diameter). Each wire was insulated such that only the metal at the tip was exposed to the solution. The twisted pair was used as the anode and cathode and a distant platinum wire (non-insulated, 500 microns in diameter) was used as a reference. FIG. 4(A) shows data acquired on a distant channel located 1 cm from the stimulating source. No discernable spikes were present on this channel demonstrating that electrical crosstalk was not present across electrical traces. FIG. 4(B) shows data recorded on an electrode contact located approximately 1 mm from the stimulating source. The average noise floor for the electrode contacts tested was 20 microV$_{p-p}$. Signal-to-noise ratios on the bench top exceeded 10:1 as seen in FIG. 4(B).

Figure 4C:
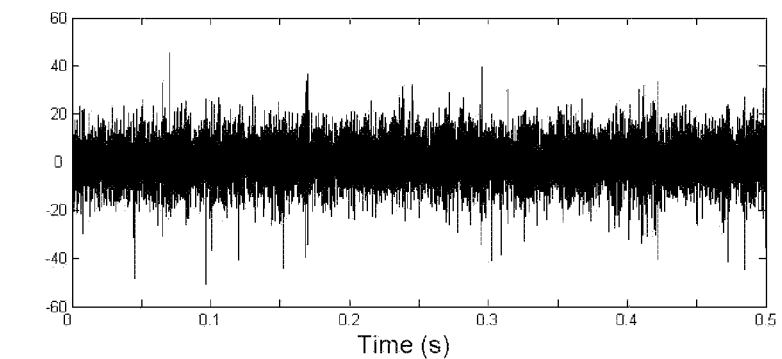

In vivo tests were conducted in anesthetized rats. Neuroprobe systems were inserted into the barrel cortex of Sprague-Dawley rats. Both local field potentials and neural spikes were acquired and saved to disk for offline analysis. FIG. 4(C) shows spike activity acquired on one channel from an implanted neuroprobe system. The average noise floor (including the neural "hash") was 30 microV$_{p-p}$. Average signal-to-noise ratios were approximately 5:1 in recordings collected from rat barrel cortex, as shown in FIG. 4(C).

Each of the references identified herein is hereby incorporated by reference as though fully set forth herein.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

What is claimed is:

1. A method of making a neuroprobe system, comprising the steps of:
   providing a carrier;
   providing a flexible planar microelectrode array including:
      providing a substrate including a plurality of conductive interconnects disposed on the substrate and disposed between layers of dielectrics;
      forming a plurality of electrode sites on the substrate such that at least some electrode sites are in contact with a corresponding interconnect, and
      forming a plurality of bond pads, at least some of which are in contact with a respective interconnect;
   folding the planar microelectrode array; and
   coupling the planar microelectrode array to the carrier.

2. The method of claim 1, wherein providing a carrier includes providing a carrier with a lumen.

3. The method of claim 2, wherein providing a carrier with a lumen includes configuring the lumen to carry fluid.

4. The method of claim 2, further including inserting a stylet into the lumen.

5. The method of claim 2, further including inserting a wire microelectrode into the lumen.

6. The method of claim 1, wherein providing a flexible planar microelectrode array includes providing a substrate with a lateral projection having an electrode site disposed thereon.

7. The method of claim 6, wherein coupling the planar microelectrode array to the carrier includes attaching the lateral projection radially to the carrier.

8. The method of claim 7, wherein folding the planar microelectrode array includes wrapping the lateral projection of the planar microelectrode array around the carrier.

9. The method of claim 1, wherein providing a substrate includes providing multiple layers of conductive interconnects, each layer being separated by a dielectric layer.

10. The method of claim 1, wherein forming a plurality of electrode sites includes opening an aperture in a dielectric layer to form a recess and filling the recess with a first metal.

11. The method of claim 10, wherein forming a plurality of electrode sites further includes depositing a second metal and patterning the second metal to form at least one electrode site.

12. The method of claim 11, wherein patterning the second metal includes patterning at least one electrode site such that the electrode site is larger than the aperture.

13. The method of claim 1, wherein providing a flexible planar microelectrode array includes providing a flexible planar microelectrode array in a serpentine shape.

14. The method of claim 13, wherein folding the planar microelectrode array includes folding the planar microelectrode array from the serpentine shape into a straight shape.

15. The method of claim 14, wherein folding the planar microelectrode array includes crimping the planar microelectrode array at one or more fold lines.

16. The method of claim 14, wherein folding the planar microelectrode array includes folding a first segment of the serpentine shape away from a second segment of the serpentine shape at a first fold line.

17. The method of claim 16, wherein folding the planar microelectrode array includes folding the first segment of the serpentine shape towards the second segment of the serpentine shape at a second fold line approximately perpendicular to the first fold line, thereby aligning the first and second segments in a straight shape.

18. The method of claim 1, wherein forming a plurality of electrode sites includes configuring a plurality of electrode sites to operate as a composite electrode site.

19. The method of claim 18, wherein configuring a plurality of electrode sites to operate as a composite electrode site includes grouping a plurality of electrode sites through connections between electrode sites.

20. The method of claim 1, wherein coupling the planar microelectrode array to the carrier includes applying an adhesive to the carrier.

* * * * *